United States Patent
Kessler et al.

(10) Patent No.: US 10,502,676 B2
(45) Date of Patent: Dec. 10, 2019

(54) DISPOSABLE WITNESS CORROSION SENSOR

(71) Applicants: Seth S. Kessler, Newton, MA (US); Christopher T. Dunn, Salem, MA (US); Yosef Stein, Sharon, MA (US)

(72) Inventors: Seth S. Kessler, Newton, MA (US); Christopher T. Dunn, Salem, MA (US); Yosef Stein, Sharon, MA (US)

( * ) Notice: Subject to any disclaimer, the term of this patent is extended or adjusted under 35 U.S.C. 154(b) by 0 days.

(21) Appl. No.: 15/639,441

(22) Filed: Jun. 30, 2017

(65) Prior Publication Data

US 2018/0003615 A1 Jan. 4, 2018

Related U.S. Application Data

(60) Provisional application No. 62/427,503, filed on Nov. 29, 2016, provisional application No. 62/357,159, filed on Jun. 30, 2016.

(51) Int. Cl.
| | |
|---|---|
| *G01N 17/04* | (2006.01) |
| *G01N 27/04* | (2006.01) |
| *G01N 17/02* | (2006.01) |
| *H04W 84/18* | (2009.01) |

(52) U.S. Cl.
CPC ............ *G01N 17/04* (2013.01); *G01N 17/02* (2013.01); *G01N 27/04* (2013.01); *H04W 84/18* (2013.01)

(58) Field of Classification Search
CPC ............................... G01N 27/048; G01N 1/04
See application file for complete search history.

(56) References Cited

U.S. PATENT DOCUMENTS

| | | | | |
|---|---|---|---|---|
| 4,326,164 A | * | 4/1982 | Victor | G01N 17/00 324/700 |
| 5,834,942 A | * | 11/1998 | De Angelis | D07B 1/025 324/522 |
| 7,244,500 B2 | | 7/2007 | Watts et al. | |
| 7,398,184 B1 | * | 7/2008 | Chen | G06Q 40/06 702/182 |
| 8,552,597 B2 | | 10/2013 | Song et al. | |
| 9,091,657 B2 | | 7/2015 | Kessler et al. | |

(Continued)

FOREIGN PATENT DOCUMENTS

| | | |
|---|---|---|
| CA | 2 864 817 A1 | 8/2013 |
| EP | 3 190 421 A1 | 7/2017 |

(Continued)

OTHER PUBLICATIONS

International Search Report and Written Opinion dated Oct. 24, 2017 in connection with International Application No. PCT/US2017/040356.

(Continued)

*Primary Examiner* — Noam Reisner
(74) *Attorney, Agent, or Firm* — Wolf, Greenfield & Sacks, P.C.

(57) ABSTRACT

Corrosion sensors are described. The corrosion sensors may include components formed from carbon nanotube structures and a corroding element formed of a material which corrodes more quickly than a target material being monitored by the corrosion sensor. The corroding material may be exposed to the environment to which the target material being monitored is exposed. The corrosion sensor may be passive, thus consuming little power.

20 Claims, 11 Drawing Sheets

(56) References Cited

U.S. PATENT DOCUMENTS

| | | |
|---|---|---|
| 9,232,475 B2 | 1/2016 | Heinzelman et al. |
| 9,372,209 B2 | 6/2016 | Iwamoto |
| 9,429,491 B2 * | 8/2016 | Bemis .................. G01L 9/065 |
| 9,480,163 B2 | 10/2016 | Kessler et al. |
| 2005/0183492 A1 | 8/2005 | Rao et al. |
| 2005/0269213 A1 | 12/2005 | Steimle et al. |
| 2006/0162431 A1 | 7/2006 | Harris et al. |
| 2007/0120572 A1 | 5/2007 | Chen et al. |
| 2008/0135614 A1 | 6/2008 | Werner et al. |
| 2008/0202930 A1 | 8/2008 | Mett |
| 2008/0204275 A1 | 8/2008 | Wavering et al. |
| 2009/0039864 A1 | 2/2009 | Gordon |
| 2009/0121872 A1 | 5/2009 | Lynch et al. |
| 2010/0008825 A1 | 1/2010 | Subramanyam |
| 2010/0097273 A1 | 4/2010 | Biris et al. |
| 2010/0320569 A1 * | 12/2010 | Narita .................. B82Y 10/00 257/537 |
| 2011/0240621 A1 | 10/2011 | Kessler et al. |
| 2012/0038377 A1 * | 2/2012 | Hamann ............... G01N 17/04 324/700 |
| 2012/0055810 A1 | 3/2012 | Zhou |
| 2012/0256492 A1 | 10/2012 | Song et al. |
| 2012/0286804 A1 * | 11/2012 | Kato .................. G01N 33/383 324/649 |
| 2013/0210154 A1 | 8/2013 | Dieckhoff et al. |
| 2013/0230429 A1 | 9/2013 | Naishadham et al. |
| 2014/0184249 A1 | 7/2014 | Saafi et al. |
| 2014/0200538 A1 * | 7/2014 | Euliano ................ A61F 13/42 604/361 |
| 2015/0317896 A1 | 11/2015 | Planton et al. |
| 2015/0330212 A1 | 11/2015 | Sassi et al. |
| 2016/0050757 A1 | 2/2016 | Diao et al. |
| 2016/0238547 A1 | 8/2016 | Park et al. |
| 2016/0302264 A1 | 10/2016 | Kessler et al. |
| 2017/0019954 A1 | 1/2017 | Kessler et al. |
| 2017/0237466 A1 | 8/2017 | Carr |
| 2017/0358854 A1 | 12/2017 | Stein |
| 2018/0139698 A1 | 5/2018 | Quinlan et al. |

FOREIGN PATENT DOCUMENTS

| | | |
|---|---|---|
| KR | 10-0839226 B1 | 6/2008 |
| WO | WO 2006/137849 A1 | 12/2006 |
| WO | WO 2008/125878 A1 | 10/2008 |

OTHER PUBLICATIONS

Kang, Carbon Nanotube Smart Materials. Thesis submitted to the Division of Research and Advanced Studies of the University of Cincinnati. 2005; 170 pages.

Kang et al., Structural Health Monitoring based on Electrical Impedance of a Carbon Nanotube Neuron. Key Engineering Materials. 2006;321-323:140-5.

Kessler, Structural Health Monitoring Capabilities. Metis Design Corporation. Powerpoint Presentation 2008, 42 pages.

International Search Report and Written Opinion dated Sep. 25, 2017 in connection with International Application No. PCT/US2017/036719.

International Preliminary Report on Patentability dated Dec. 20, 2018 in connection with International Application No. PCT/US2017/036719.

International Preliminary Report on Patentability dated Jan. 10, 2019 in connection with International Application No. PCT/US2017/040356.

Oh et al., A 116n W Multi-Band Wake-Up Receiver with 31-bit Correlator and Interference Rejection. Custom Integrated Circuits Conference (CICC), 2013 IEEE. 4 pages.

Roberts et al., A 236nW-56.5dBm-Sensitivity Bluetooth Low-Energy Wakeup Receiver with Energy Harvesting in 65nm CMOS. 2016 IEEE International Solid-State Circuits Conference. Digest of Technical Papers. 2016; pp. 450-451.

Rocheleau et al., MEMS-Based Tunable Channel-Selecting Super-Regenerative RF Transceivers. Berkeley Sensor & Actuator Center. University of California. Prepublication Data Sep. 2015; 2 pages.

Sample et al., Design of an RFID-Based Battery-Free Programmable Sensing Platform. IEEE Transactions on Instrumentation and Measurement. Nov. 2008;57(11):2608-15.

* cited by examiner

DISPOSABLE WITNESS CORROSION SENSOR

RELATED APPLICATIONS

This Application claims priority under 35 U.S.C. § 119(e) to U.S. Provisional Application Ser. No. 62/357,159, entitled "DISPOSABLE WITNESS CORROSION SENSOR" filed on Jun. 30, 2016, which is herein incorporated by reference in its entirety.

This Application claims priority under 35 U.S.C. § 119(e) to U.S. Provisional Application Ser. No. 62/427,503, entitled "DISPOSABLE WITNESS CORROSION SENSOR" filed on Nov. 29, 2016, which is herein incorporated by reference in its entirety.

FIELD OF THE DISCLOSURE

The present application relates to corrosion sensors.

BACKGROUND

One or more states of a target material may change when the target material is exposed to certain environmental conditions. For example, a target material may be subject to corrosion when exposed to certain temperature, mechanical vibration, humidity or moisture conditions over a period of time, such that physical and chemical characteristics of the target material may change over the same period of time. A sensor apparatus may be used to monitor a state of the target material.

SUMMARY OF THE DISCLOSURE

Corrosion sensors are described. The corrosion sensors may include components formed from carbon nanotube structures and a corroding element formed of a material which corrodes more quickly than a target material being monitored by the corrosion sensor. The corroding material may be exposed to the environment to which the target material being monitored is exposed. The corrosion sensor may be passive, thus consuming little or no power.

According to some embodiments, a low power wireless sensor system for monitoring a state of corrosion of a target material is provided. The low power wireless sensor system comprises a housing, a witness corrosion sensor disposed within the housing. The witness corrosion sensor comprises first resistive arm having a first resistance and a second resistive arm having a second resistance. The first resistive arm comprises a sensor element connected in parallel with at least one resistor comprising carbon nanotubes, and the second resistive arm comprises at least one resistor comprising carbon nanotubes. The low power wireless sensor system also comprises processing circuitry disposed within the housing that is configured to measure a difference between the first resistance and the second resistance and to determine a state of corrosion of the target material based on a difference between the first resistance and the second resistance. The low power wireless sensor system further comprises an energy storage module disposed within the housing that is configured to store electrical energy and to provide power to at least a portion of the processing circuitry, as well as a wireless communication module coupled to the processing circuitry. The wireless communication module is configured to wirelessly communicate information external to the housing.

According to some embodiments, a wireless sensor system for monitoring a state of corrosion of a target material is provided. The wireless sensor system comprises a passive sensor apparatus. The passive sensor apparatus comprises a first resistive arm with a first resistance and a second resistive arm with a second resistance. The first resistive arm comprises a sensor element connected in parallel with at least one resistor comprising carbon nanotubes. The second resistive arm comprises at least one resistor comprising carbon nanotubes. The wireless sensor system further comprises a circuit configured to measure a difference between the first resistance and the second resistance and a processor configured to determine a state of corrosion of the target material based on the difference between the first resistance and the second resistance measured by the circuit. The wireless sensor system also comprises an energy storage module disposed within the housing and configured to store electrical energy and to provide power to at least a portion of the circuit. The wireless sensor system further comprises transmit circuitry coupled to the circuit and configured to transmit corrosion information.

According to some embodiments, a method is provided for operating a low power wireless sensor system. The method comprises measuring, with processing circuitry disposed in a housing of the low power wireless sensor system, a difference between a resistance of a first resistive arm and a resistance of a second resistive arm of a witness corrosion sensor comprising the first resistive arm and the second resistive arm. The first resistive arm comprises a sensor element connected in parallel with at least one resistor comprising carbon nanotubes, and the second resistive arm comprises at least one resistor comprising carbon nanotubes. The method further comprises determining, with the processing circuitry, a state of a target material based at least in part on the measured difference. The method further comprises providing, with an energy storage module disposed in the housing and configured to store electrical energy, power to at least a portion of the processing circuitry. The method further comprises wirelessly communicating, with a wireless communication module, information external to the housing.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
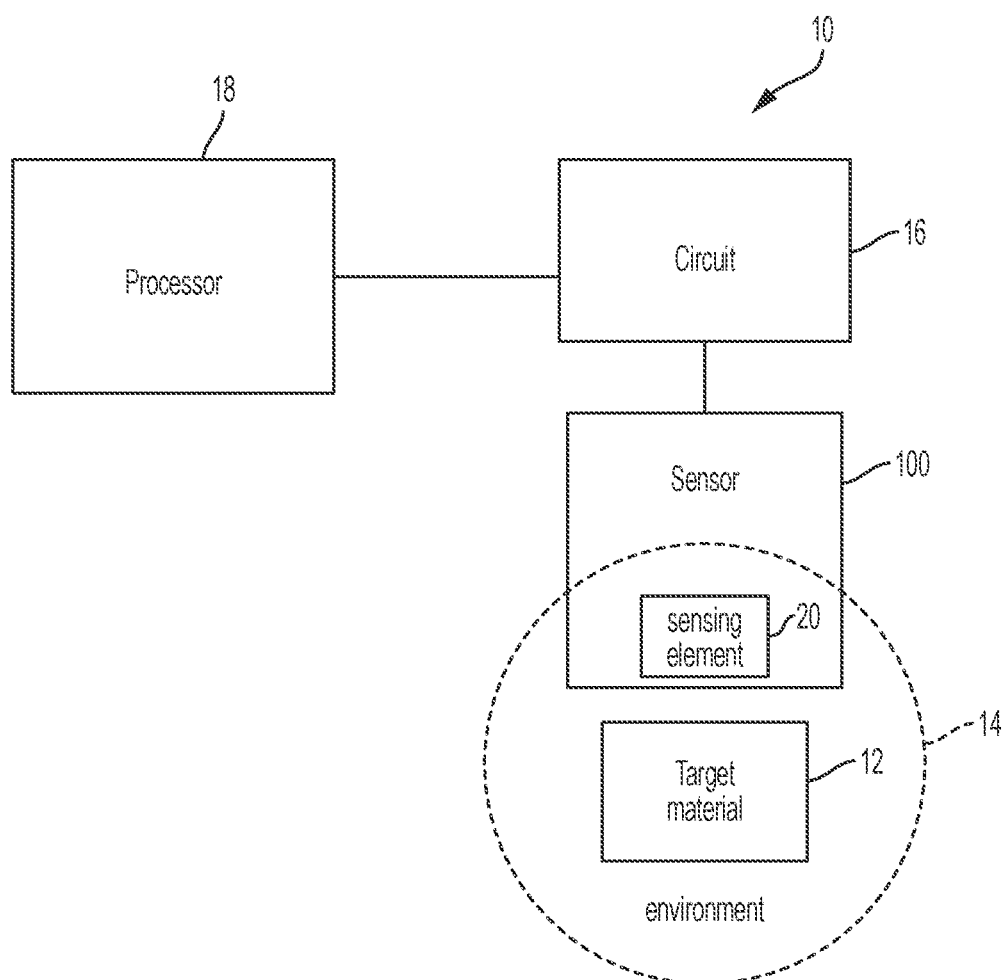
FIG. 1 is a block diagram of an exemplary sensor system 10, according to aspects of the present application.

Aspects of the present application provide a sensor apparatus for monitoring a state of a target material disposed in an environment. The sensor apparatus comprises a sensing element with a characteristics whose value varies in a manner indicative of the state of the target material. The sensor element, as well as additional components of the sensor apparatus, may be formed of carbon nanotubes (CNTs). In some embodiments, the sensing element of the sensor apparatus is disposed within the same environment as the target material such that the sensing element experiences substantially the same environmental conditions as the target material, including but not limited to temperature, acoustic or mechanical vibration, humidity or moisture variations. In some embodiments, the sensing element comprises a material with a variable electrical resistance that varies predictably when the state of the material changes due to exposure to the environment, which can be used to indicate a change of the state of the target material in the same environment without directly measuring the target material. In at least some embodiments, the sensor apparatus may be a self-contained, passive sensor apparatus containing a sensing element formed of CNTs and other components suitable for operation of the sensor apparatus including communication of the sensor apparatus with external devices.

According to some aspects of the present application, the sensor apparatus may comprise a plurality of resistors configured to have resistance values based at least in part on a change in state of the sensing element in the sensor apparatus, which is indicative of the state of a target material disposed within the same environment of the sensing element. The inventors have recognized and appreciated that resistor elements in a sensor apparatus may be subject to background drift over a period of time and overall signals measured may comprise a sensor signal superimposed on the background drift. The background drift may be caused by, for example, internal temperature and humidity changes that are unrelated to the environment of the target material is disposed in. Periodic calibration may correct sensor background drift prior to using the sensor apparatus to monitor a state of the target material, although performing an off-line calibration may increase operational cost, interrupt continuous monitoring and in some cases, not be possible when the sensor apparatus is deployed in a difficult to access location. The inventors have recognized and appreciated that comparing two resistive arms within the same sensor apparatus that are subject to substantially the same background drift can effectively suppress or reject the common background drift while accentuating desired sensor signal, thus increasing the signal to background ratio without the need to take the sensor apparatus offline to perform a calibration. In some embodiments, the sensor apparatus comprises a first resistive arm and a second resistive arm. The first resistive arm comprises the sensor element and has a first electrical resistance that varies when the state of a target material changes due to exposure to the environment. The second resistive arm comprises one or more resistors with a second electrical resistance that is not responsive to changes in the state of the target material, but is configured to be a reference resistor having substantially the same background drift as the first resistive arm. Therefore the first electrical resistance and the second electrical resistance, when combined by for example subtracted the second electrical resistance of the reference resistor from the first electrical resistance, yield an electrical resistance value that is indicative of the state of the target material.

According to an aspect of the present application, the sensor apparatus is a corrosion sensor for monitoring a state of corrosion of a target material. The sensor apparatus comprises a sensing element with a variable electrical resistance that varies based in part on the state of corrosion of the target material. In some embodiments, the sensing element is disposed within the same corroding environment as the target material, and comprises a corroding element that has a known relationship between resistance and state of corrosion as it corrodes when exposed to the same corroding environment. In one non-limiting example, the corroding element may comprise a metal film whose thickness decreases when the metal film is progressively corroded, leading to an increase of the electrical resistance of the metal film. Therefore a state of corrosion of the corroding element in the sensing element may be monitored by measuring its resistance, to represent a state of corrosion of the target material. According to some embodiments, the state of corrosion of a material may be the percentage of material corroded compared to a reference state in time, a percentage change of a material characteristic such as electrical resistance compared to a reference state in time, an estimated lifetime of a corroded material, or any other suitable characteristic measures of a state of corrosion for a material.

The inventors have appreciated and recognized that carbon nanotubes (CNTs) are a material having strong covalent carbon-carbon bonds that are chemically stable, resistive to corrosion and electrically conductive. In some embodiments, elements of the corrosion sensor may comprise carbon nanotubes (CNTs). For example, a corrosion sensor may implement components formed from carbon nanotubes (CNT). In some embodiments, the corrosion sensor comprises a first resistive arm comprising a sensor element connected in parallel with at least one resistor comprising carbon nanotubes, and a second resistive arm comprising at least one resistor comprising carbon nanotubes. The first resistive arm comprises the sensor element and has a first electrical resistance that varies when the state of a target material changes due to exposure to the environment. The second resistive arm comprises one or more resistors with a second electrical resistance that is not responsive to the state of corrosion of the target material, but is configured to have substantially the same background drift as the first resistive arm. Therefore the first electrical resistance and the second electrical resistance, when combined by for example subtracted from one another, yield an electrical resistance value that is indicative of the state of corrosion of the target material.

According to an aspect of the present application, a corrosion sensor may be provided that includes a corroding element configured to be exposed to the same environmental conditions (e.g., same pressure and/or temperature and/or humidity) as a target material to monitor the state of corrosion of the target material, and thus the sensor may also be referred to as a witness corrosion sensor. The corrosion sensor may have an electrical resistance which changes as the corroding element corrodes. By monitoring the resistance of the corrosion sensor, the corrosion of the corroding element may be determined and therefore the corrosion of the target material may be determined. In some embodiments, the corroding element may be configured to corrode faster than the target material, such that the corrosion sensor may be used to alert the state of corrosion of the target material prior to the target material being completely corroded.

According to an aspect of the present application, the witness corrosion sensor may be a passive sensor. As used herein, a passive sensor is used to refer to a sensor that lacks a power supply. Power may instead be harvested or supplied from external components, for example to read out the sensor's condition and/or to reconfigure the sensor functionality. In some embodiments, the witness corrosion sensor may include a plurality of resistors, including a corroding element of the sensor. A passive witness corrosion sensor may be placed in the vicinity of a target material to be monitored, and only be queried to measure one or more resistance values indicative of the state of corrosion of the target material occasionally. For example, a passive witness corrosion sensor may only need to be measured once every day, once every week, once every month, or at any suitable regular or random interval. Because the sensor lacks active components in such embodiments, it may consume little power and can operate for a long period of time such as several months or several years, and thus be suitable for ultra-low power (ULP) applications. For instance, the passive witness corrosion sensor may be used in a ULP sensor system.

According to an aspect of the present application, a sensor system may be provided for monitoring a state of corrosion of a target material. The sensor system comprises a sensor apparatus such as any of the sensor apparatus discussed above. In some embodiments, the sensor system comprises a passive sensor including a plurality of resistors. The passive corrosion sensor comprises a first resistive arm comprising a sensor element connected in parallel with at least one resistor comprising carbon nanotubes, and a second resistive arm comprising at least one resistor comprising carbon nanotubes. The first resistive arm comprises the sensor element and has a first electrical resistance that varies when the state of a target material changes due to exposure to the environment. The second resistive arm comprises one or more resistors with a second electrical resistance that is not responsive to the state of corrosion of the target material, but is configured to have substantially the same background drift as the first resistive arm. In some embodiments, the passive corrosion sensor does not comprise a power source. The sensor system further comprises a circuit configured to measure a difference between the first resistance and the second resistance. The circuit also comprises a power source to provide voltage and/or current to the passive corrosion sensor during measurements. The sensor system further comprises a processor configured to determine the state of corrosion of the target material based at least in part on the difference between the first resistance and the second resistance measured by the circuit. In some embodiments, the sensor system is configured to determine and monitor the state of corrosion substantially in real-time. In some other embodiments, the sensor system is configured to measure the state of corrosion occasionally and only at a predetermined interval to reduce power consumption. The measured values may be saved in a memory in the sensor system to be extracted later.

According to an aspect of the present application, a sensor apparatus may further comprise circuitry within the sensor. In one example, the sensor apparatus may be a wireless sensor apparatus comprising control circuit configured to control wireless communication of a state of a target material being monitored based on a difference between a first resistance of a first resistive arm and a second resistance of a second resistive arm within the wireless sensor apparatus.

According to an aspect of the present application, the passive witness corrosion sensor may be manufactured at a low cost and may be disposable.

FIG. 1 is a block diagram of an exemplary sensor system 10, according to aspects of the present application. The sensor system 10 comprises a processor 18, a circuit 16, a sensor 100 having a sensing element 20, a target material 12 and an environment 14.

In the sensor system 10, the sensor 100 may be a sensor apparatus comprising a plurality of resistors configured to have resistance values based at least in part on a change in state of the sensing element 20, which is indicative of a state of the target material 12 disposed within the same environment 14 of the sensing element 20. At least a portion of components of sensor 100 are not exposed to the environment 14.

In some embodiments, the sensor 100 is a corrosion sensor configured for monitoring a state of corrosion of the target material 12. The target material may be, for example, a steel beam of a building structure, a metal component of an industrial equipment or a medical instrument, a part of a vehicle such as automobile, airplane or spacecraft, a component of a consumer electronic device, a wearable device, a farming or a food processing equipment, although it should be appreciated that other target materials and structures may be monitored with a corrosion sensor of the types described herein. In some embodiments, the sensor 100 is a witness corrosion sensor with the sensing element 20 placed in close vicinity to the target material. For example, a sensing element 20 may be attached to the exterior of a steel beam and exposed to the same weather environment of the steel beam been monitored, while at least some components other than the sensing element 20 inside the sensor 100 are protected from exposure to the weather environment. Any suitable method may be used to selectively expose the sensing element 20 to the environment 14, such as but not limited to placing components of sensor 100 inside a sealed enclosure while exposing sensing element 20 outside of the enclosure. In some embodiments, the sensing element 20 may comprise a corroding element formed from a metal film that can corrode in the environment 14 and have a known electrical resistance versus the state of corrosion. Therefore a measurement of the resistance of the corroding element inside the sensing element 20 may provide an indication of the corrosion of the corroding element, which can be used to infer the state of corrosion of the target material 12.

In some embodiments, sensor 100 may be a passive sensor that does not comprise a power source. The sensor system 10 comprises a circuit 16 configured to communicate with the sensor 100 to perform measurements to monitor a state of the target material 12. The circuit 16 may also communicate with the sensor 100 to adjust reconfigurable parameters of the sensor 100, such as I/O operation with non-volatile memory element, or programming a reprogrammable logic element (both not shown) within the sensor 100. The circuit 16 also comprises a power source to provide voltage and/or current to the passive sensor 100 during measurements and communications. The sensor system 10 further comprises a processor 18 configured to determine the state of the target material based at least in part on data transmitted from the sensor 100 to the circuit 16. Any suitable communication protocol may be used for processor 18 to communicate with the circuit 16. Processor 18 may be a local processor attached to the circuit 16, or in some embodiments processor 18 may be based on the cloud and communicate with the circuit 16 using a wired or wireless interface.

It should be appreciated that although FIG. 1 shows the processor 18 and circuit 16 to be separate components from the sensor 100, embodiments of the present application are not limited to such an arrangement. In some embodiments, the sensor 100 may be a sensor apparatus that comprises one or more processors and/or circuits. In some embodiments, sensor 100 is a wireless sensor apparatus comprising control circuit configured to control wireless communication of a state of the target material.

Figure 2:
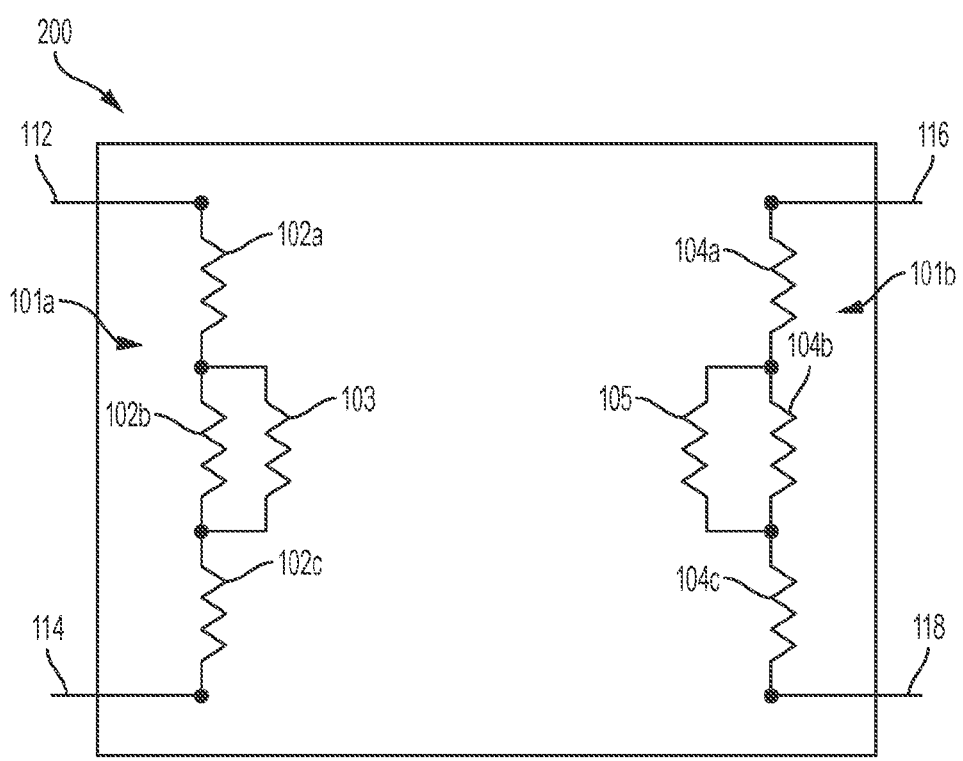
FIG. 2 is a schematic circuit diagram of an exemplary corrosion sensor 200, according to aspects of the present application.

FIG. 2 is a schematic circuit diagram of an exemplary corrosion sensor 200, according to aspects of the present application. The corrosion sensor 200 includes two resistive arms, 101a and 101b. The resistive arm 101a includes terminals 112, 114, resistors 102a, 102b, 102c, and corroding element 103. The resistive arm 101b includes terminals 116, 118, resistors 104a, 104b, and 104c, and optionally resistor 105.

In the embodiment in FIG. 2, resistive arm 101a comprises resistors 102a-102c and 103 connected between terminals 112 and 114. A first node of resistor 102a is connected to terminal 112. A second node of resistor 102a is connected to a first node of resistor 102b. A second node of resistor 102b is connected to a first node of resistor 102c. A second node of resistor 102c is connected to terminal 114. Resistor 103 is connected to resistor 102b in parallel.

In the embodiment in FIG. 2, resistive arm 101b comprises resistors 104a-104c and optionally resistor 105 connected between terminals 116 and 118. A first node of resistor 104a is connected to terminal 116. A second node of resistor 104a is connected to a first node of resistor 104b. A second node of resistor 104b is connected to a first node of resistor 104c. A second node of resistor 104c is connected to terminal 118. Optionally, resistor 105 is provided and is connected to resistor 104b in parallel.

One or more of the resistors 102a-102c and 104a-104c may be formed from CNT structures. As used herein, CNT structures refer to material components that comprise carbon nanotubes with a CNT weight percentage of between 1% and 100%. CNT structures may be a CNT composite with a network of interconnecting CNTs embedded in a matrix of polymer resin material such that the high mechanical strength, low weight and high electrical conductivity are obtained. In some embodiments, CNT structures may be formed as a thin film and applied using a polymer precursor solution mixed with a CNT dispersant, which when dried forms a thin film. The thin film method may be applied to a surface of various shape or dimensions by spray or spin coating, thus reducing the cost of manufacturing. In some embodiments, the resistors 102a-102c and 104a-104c are formed substantially from CNT structures. The resistors 102a-102c and 104a-104c may have any suitable resistances, and in one embodiment all have equal resistances.

According to some embodiments, the corroding element 103 may be formed of a material which corrodes as fast as, or faster than, the target material being monitored by the sensor 200. For example, the corroding element 103 may be formed of copper in an embodiment, although other materials are possible, such as coating materials used to coat automotive or airplane components. By using a material which corrodes more quickly than the target material being monitored, it may be possible to assess and predict corrosion of the target material prior to such material failing or otherwise reaching an undesirable level of corrosion. In some embodiments, the corroding element 103 may be the only element of corrosion sensor 100 exposed to the same environment as the target material. The other components may be housed separately or otherwise protected from the environment.

In operation, the witness corrosion sensor 200 may be disposed on or in proximity to the target material being monitored so that the corroding element 103 experiences substantially the same conditions as the target material. For example, in industrial applications the target material may be a steel beam of a building, although it should be appreciated that other target materials and structures may be monitored with a witness corrosion sensor of the types described herein. A voltage may be applied to the resistive arm 101a between the terminals 112 and 114, and the current through the resistive arm 101a is monitored through the terminal 112 or 114. As the corroding element 103 corrodes its resistance will increase, thus changing the resistance of the resistive arm 101a. In some embodiments, the resistive arm 101a may be a first resistive arm with a first resistance as measurable between terminals 112 and 114. In some embodiments, the resistive arm 101b may be a second resistive arm with a second resistance as measurable between terminals 116 and 118. Information about the changing resistance of the resistive arm 101a may be stored, transmitted to a circuit such as circuit 16 as shown in FIG. 1, which may be an external device or the Cloud, processed by a processor such as processor 18 as shown in FIG. 1 to assess a rate of corrosion and predict future corrosion, or otherwise handled in a desired manner.

As a non-limiting example, each of resistors 102a-102c may be a resistor formed from CNT structures and having a resistance R. The corroding element 103 may be formed of a material having a significantly lower resistance, such as copper in a non-limiting example. Thus, when intact and in an un-corroded state, the corroding element 103 may serve as a short circuit around resistor 102b, meaning that the first resistance of resistive arm 101a may be equal to 2R. As the corroding element 103 corrodes during operation of the sensor 100, its resistance may increase. When the corrosion of corrosion element 103 reaches a certain point, the corroding element 103 may effectively be an open circuit. Thus, the first resistance of the resistive arm 101a may become 3R. Monitoring the change in the first resistance of the resistive arm 101a may provide an indication of the corrosion of the corroding element 103 and therefore the target material, the corrosion of which the sensor 200 is monitoring.

The resistive arm 101b may be used as a reference resistor to equalize or normalize the resistance of the resistive arm 101a. In an example, resistive arm 101b may be used to form a resistive bridge in combination with resistive arm 101a. That is, the illustrated witness corrosion sensor 200 may optionally include or be part of a larger electrical circuit configured to allow monitoring of the resistance of resistive arm 101a and provide an improved signal to background ratio. In one embodiment, resistive arms 101a and 101b may be arms of a Wheatstone bridge. The bridge may be used to monitor and provide an indication of the resistance of the resistive arm 101a and therefore of the corrosion of corroding element 103. In some embodiments, resistor 105, which may be a non-corroding resistor, (e.g., a CNT resistor), may be used as a reference for assessing the corrosion of corroding element 103. In such embodiments, the change in resistance associated with corroding element 103 may be compared with that of resistor 105.

In some embodiments, the first resistance of the resistive arm 101a and the second resistance of resistive arm 101b may depend on the environmental conditions, such as temperature and humidity. To compensate for variations in resistance caused by temperature and/or humidity variations, the resistance of the resistive arms may be combined in any suitable way. For example, the resistance of one resistive arm may be subtracted from the resistance of the other resistive arm in some embodiments. In this way, the temperature and/or humidity dependence may be limited. In some embodiments, resistors 104a, 104b and 104c may be covered (e.g., plated) with a non-corroding material. Additionally, or alternatively, resistors 102a, 102b and 102c may be covered (e.g., plated) with a non-corroding material. Covering the resistors with non-corroding material may ensure that variations in resistance of such resistors are caused by variations in environmental conditions, rather than by corrosion.

Figure 3:
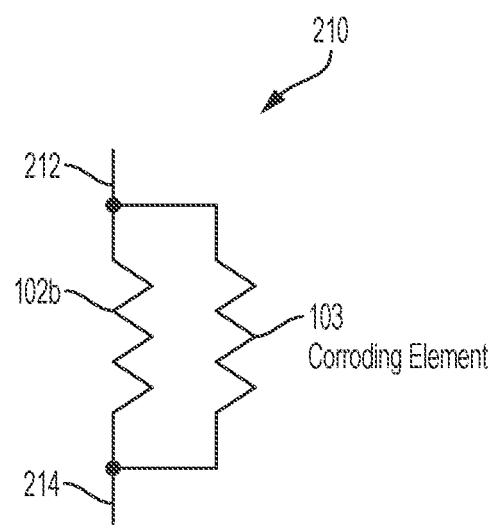
FIG. 3 is a schematic circuit diagram showing a subset 210 of the components of witness corrosion sensor 200, according to an aspect of the present application.

FIG. 3 is a schematic circuit diagram showing a witness corrosion sensor 210, according to an aspect of the present application. The subset 210 includes terminals 212, 214 and resistors 102b, 103.

In the circuit in FIG. 3, the witness corrosion sensor 210 includes a single resistor 102b in parallel with the corroding element 103. As with the witness corrosion sensor 200 of FIG. 2, corrosion of the corroding element 103 will alter the resistance of the illustrated structure, and this changing resistance may be monitored to assess the corrosion of the corroding element, thereby giving an indication of the corrosion of the target material.

Referring back to the embodiment illustrated in FIG. 2, the witness corrosion sensor 200 may provide greater detectability of the changing resistance of the corroding element 103 than the configuration of the witness corrosion sensor 210 in FIG. 3. The resistors 102a-102c may have relatively small resistances, for example if they are implemented using CNT structures. Thus, including three such resistors 102a-102c, rather than a single resistor 102b as in FIG. 3, may increase the total resistance of the resistive arm 101a and therefore facilitate operation of the circuit. Also, as described previously, the witness corrosion sensor 100, with the second resistive arm 101b, may facilitate the use of a bridge circuit or other circuit for detecting the change in resistance.

Figure 4:
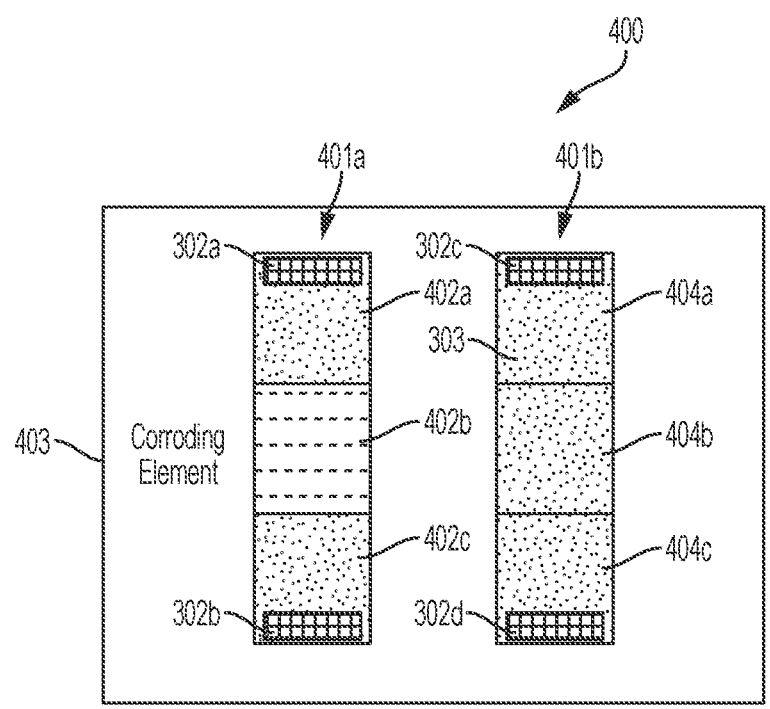
FIG. 4 is a schematic diagram showing a top view of an exemplary passive witness corrosion sensor 400, according to an aspect of the present application.

FIG. 4 is a schematic diagram showing a top view of an exemplary passive witness corrosion sensor 400, according to an aspect of the present application. In the diagram in FIG. 4, witness corrosion sensor 400 includes a first resistive arm 410a with electrical contacts 302a, 302b, resistors 402a, 402b, 402c and corroding element 403, a second resistive arm 401b with electrical contacts 302c, 302d, resistors 404a, 404c and 404b and a strip of CNT material 303.

The first resistive arm 401a may be formed by a strip of CNT material 301 making up resistors 402a, 402b, and 402c. The corroding element 403 may be disposed on the strip of CNT material. Electrical contacts 302a and 302b may be provided to electrically contact the strip of CNT material 301.

Similarly, the second resistive arm 401b may be formed by a second strip of CNT material 303 making up resistors 404a-404c. Electrical contacts 302c-302d may be provided to electrically contact the strip of CNT material 303. In some embodiments, some or all of the resistors 402a, 402b, 402c, 404a, 404b, and 404c may be plated with a non-corroding material.

Figure 5A:
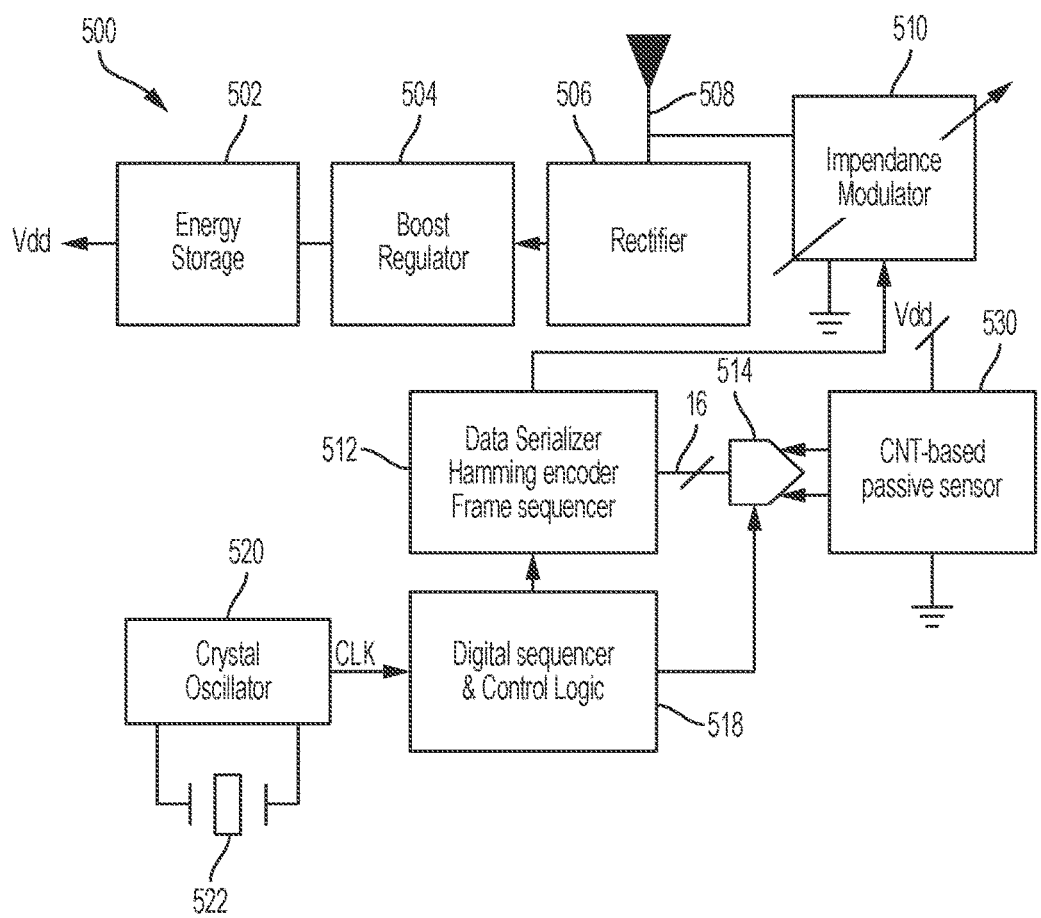
FIG. 5A is a block diagram showing an exemplary sensor system 500, according to an aspect of the present application.

FIG. 5A is a block diagram showing an exemplary sensor system 500, according to an aspect of the present application. The sensor system 500 shown in the embodiment in FIG. 5 includes an energy storage device 502, a regulator 504, a rectifier 506, antenna 508, an impedance modulator 510, a formatting and encoding circuit 512, analog-to-digital converter (ADC) 514, passive sensor 530, controller 518, oscillator 520, and resonator 522.

Passive sensor 530 may be the sensor apparatus 100 as shown in FIG. 1. In some embodiments, passive sensor 530 may be the witness corrosion sensors of FIG. 2 and includes a CNT-based passive sensor, according to an aspect of the present application.

In some embodiments, sensor system 500 is a low-power wireless sensor system. Energy storage device 502 is a power source that provides power to at least some components of the sensor system 500. In one example, energy storage device provides a voltage Vdd that is connected to the passive sensor 530. Energy storage device 502 may be connected to an external power supply (not shown) that provides a suitable voltage and current for operation of the sensor system 500, although such an external power connection is not required. In one embodiment, energy storage device 502 may comprise a battery or capacitor for storing energy. In yet another embodiment, energy storage device may additionally comprise one or more energy harvesters to recharge a battery or capacitor, such that the sensor system 500 can operate for a prolonged period of time without the need to be connected to an external power source such as a power outlet to recharge the battery or capacitor inside the energy storage device 502. The energy harvester may be a mechanical harvester that converts mechanical-acoustic energy such as vibration or human motion into electricity, a thermoelectric harvester that converts temperature gradient such as temperature difference between different parts of the sensor system 500 into electricity, a solar energy or photovoltaic harvester that converts ambient light into electricity, or an electrochemical energy harvester that converts electrochemical potential differences in the system environment into electricity.

The regulator 504 and rectifier 506 are configured to regulate an output of the energy storage device 502 and rectify the regulated output to provide one or more voltage/current sources suitable for operation of the sensor system 500.

At least some of the components of the passive sensor system 500 are fabricated from carbon nanotubes. In some embodiments, the energy storage device 502, rectifier 506, antenna 508, and passive sensor 100 comprise or are formed from CNTs. In some embodiments, these components may be formed from a common piece of CNT nanostructured material, for example occupying different areas or vertical positions within the material. In some embodiments, vertical aligned CNT nanostructures are used, such that the components are formed at different levels or layers of a piece of CNT nanostructure and are vertically interconnected by CNTs. Forming one or more components of the passive sensor system 500 from CNTs facilitates achieving a small device size, on the nanoscale. While in the illustrated embodiment some of the components are formed from carbon nanotubes, the various aspects of the present application are not limited in this respect. For example, the various components in FIG. 5 may be formed in other ways.

The energy storage device 502 is in some embodiments a CNT-based energy storage device. For example, energy storage device 502 may be a supercapacitor formed from CNTs.

The regulator 504 may be any suitable type of regulator as the various aspects described herein are not limited to use with a particular type of regulator. In some embodiments, the regulator may be formed from CNTs.

The rectifier 506 may be formed from CNT nanostructure in some embodiments.

The antenna 508 may be a carbon nanotube antenna in some embodiments. The combination of the antenna 508 and impedance modulator 510 may provide a variable impedance antenna, allowing for the passive sensor system 500 to communicate wirelessly using backscattering. Thus, as shown, the passive sensor system 500 may lack a transmitter, and instead may use a received radio frequency (RF) signal, such as a 2.4 GHz continuous wave (CW) signal. Thus, the antenna 508 may be a 2.4 GHz antenna in some embodiments, although other frequencies may be used. In some embodiments, the antenna 508 may be flexible, allowing it to conform to a structure on which the passive sensor system 500 is placed. For example, the passive sensor system may be placed on a motor shaft, and the antenna 508 may conform to the shaft.

Because transceivers may consume a relatively large amount of power, constructing the passive sensor system 500 without a transceiver provides a meaningful reduction in power consumption of the system.

The formatting and encoding circuit 512 may perform formatting and encoding functions. In some embodiments, the formatting and encoding circuit 512 may serialize data, encode using Hamming encoding, and sequence frames to be transmitted. However, alternative or additional functions are possible.

The controller 518 may be a digital sequencer with control logic, and may receive a clock signal "CLK" from an oscillator 520 (e.g., a crystal oscillator) having a resonator 522 (e.g., a crystal resonator). The controller 518 may provide outputs to both the formatting and encoding circuit 512 and the ADC 514. It should be appreciated that the controller 518 is, in at least some embodiments, not a processing core. Rather, the controller 518 may be relatively simple, for example being a shift register with control logic. Such a construction may consume less power than a microprocessor core, facilitating operation of the passive sensor system 500.

Figure 5B:
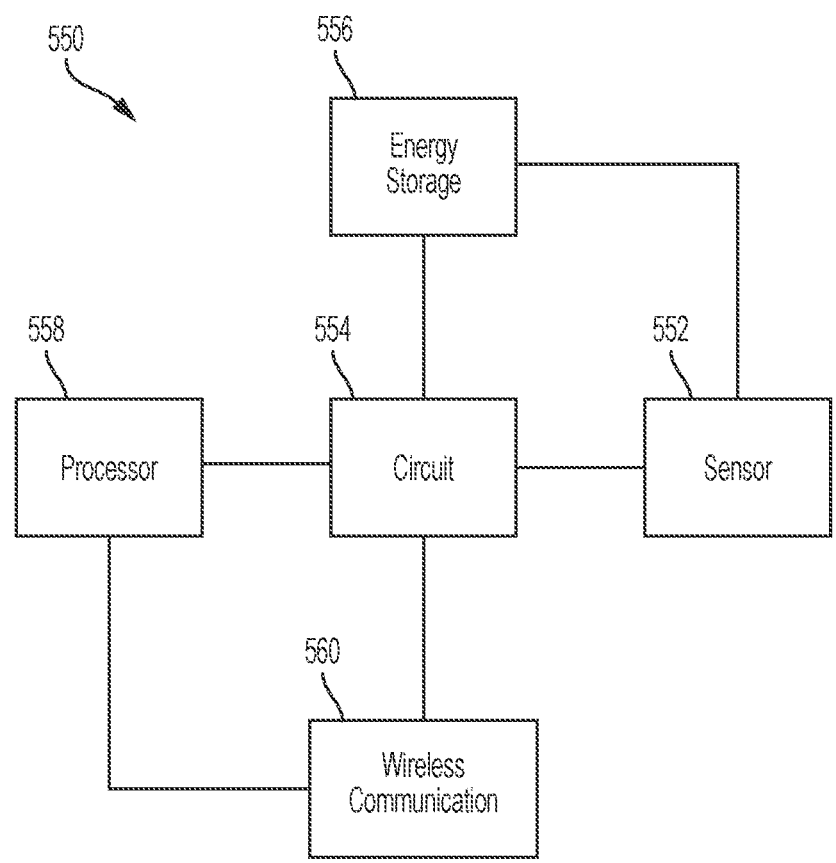
FIG. 5B is a block diagram showing an exemplary wireless sensor system 550, according to an aspect of the present application.

While the sensor system 500 shown in FIG. 5A represents an exemplary embodiment, a more generalized embodiment for a wireless sensor system is shown in FIG. 5B. FIG. 5B is a block diagram showing an exemplary wireless sensor system 550, according to an aspect of the present application. In the diagram shown in FIG. 5B, a wireless sensor system 550 includes a sensor 552, a circuit or processing circuit 554, an energy storage module 556, one or more processors 558 and a wireless communication module 560. One or more of the components of the wireless sensor system 550 may be disposed in a housing (not shown). For example, the sensor 552, circuit 554, energy storage module 556, wireless communication module 560 and processor 558 may be housed in a housing. Optionally or additionally, a processor 558 may be provided outside the housing, for example as a remote processor in the cloud that are coupled to the circuit 554 and/or the wireless communication module 560 using any suitable communication means.

Figure 6:
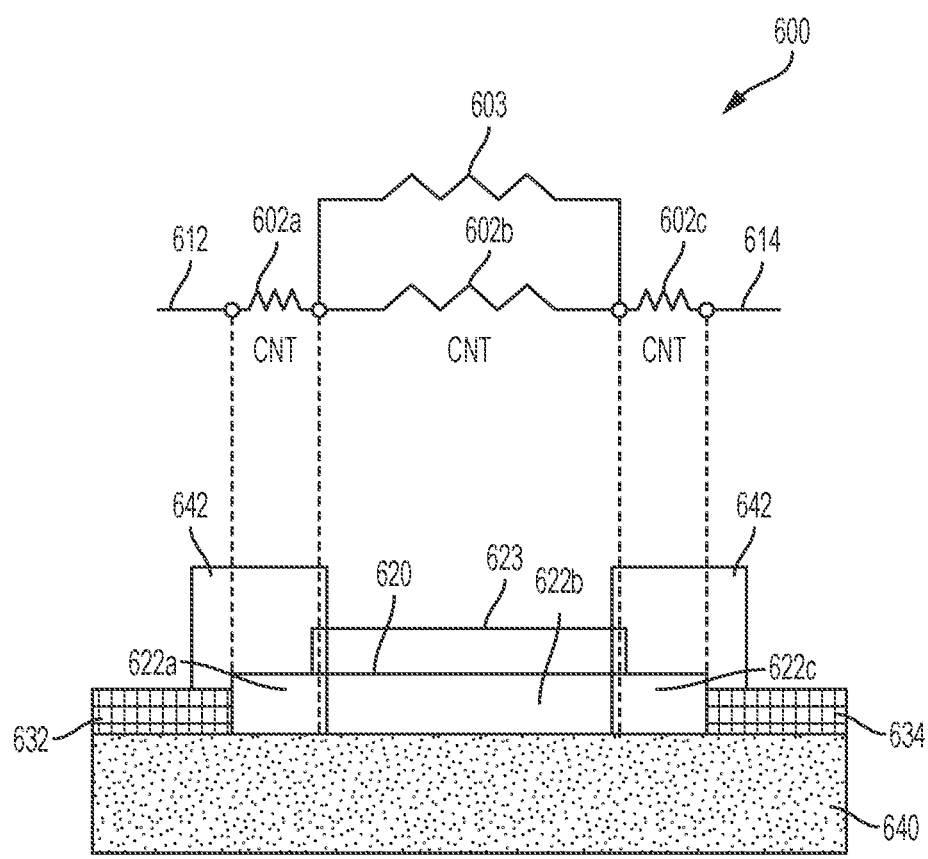
FIG. 6 is a schematic illustration showing a circuit diagram and a plan view diagram of an exemplary corrosion sensor 600, according to an aspect of the present application.

FIG. 6 is a schematic illustration showing a circuit diagram and a plan view diagram of an exemplary corrosion sensor 600, according to an aspect of the present application.

As shown in the circuit diagram in FIG. 6, corrosion sensor 600 includes resistors 602a, 602b, 602c, 603 and terminals 612, 614. Corrosion sensor 600 is similar in some ways to the first resistive arm 101a of corrosion sensor 200 shown in FIG. 2, and comprises resistors 602a-602c and corroding element 603 connected between terminals 612 and 614. A first node of resistor 602a is connected to terminal 612. A second node of resistor 602a is connected to a first node of resistor 602b. A second node of resistor 604b is connected to a first node of resistor 604c. A second node of resistor 604c is connected to terminal 614. Corroding element 603 is provided and is connected to resistor 602b in parallel. A resistance between terminals 612 and 614 may be used to measure the resistance of corroding element 603 which is indicative of a state of corrosion of a target material (not shown) in the vicinity of the corroding element 603 when the corroding element and the target material is exposed to the same environment. It should be appreciated that although sensor 600 is shown to have only one resistive arm, an optional second resistive arm may be provided as reference resistor with a second resistance to be combined with the first resistance of the resistive arm between 612 and 614 to monitor corrosion state of a target material.

The plan view diagram in FIG. 6 shows an exemplary implementation of corrosion sensor 600 as shown in the circuit diagram in FIG. 6 that includes CNT structure 620 with segments 622a, 622b, 622c, copper layer 623, gold contact electrodes 632, 634, substrate 640 and passivation 642. In some embodiments, the corrosion sensor 600 may be fabricated from a CNT structure 620 on a substrate 640. Electrodes 634 are deposited on both ends of the CNT structure 620 to form terminals 612 and 614. Passivation layers such as photoresist 642 are patterned and deposited in the regions near the two ends of the CNT structure to define CNT segments 622a and 622c that form resistors 602a and 602c. A corroding element may be formed by depositing copper in the CNT segment 622b that is exposed from passivation, thus forming a corroding element 603 in parallel with resistor segment 602b.

Figure 7:
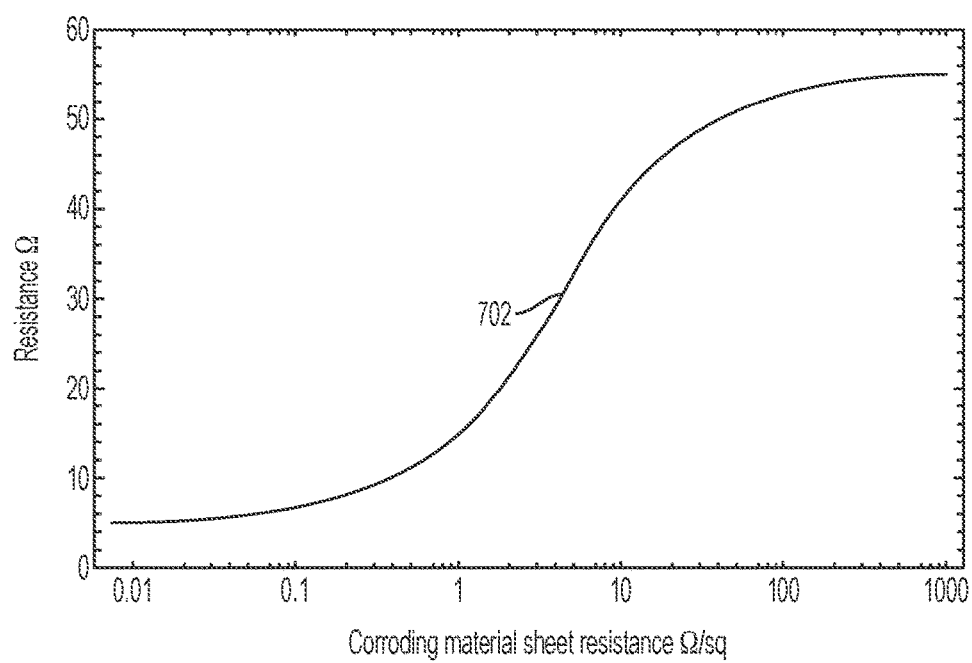
FIG. 7 is a graph showing resistance of a witness corrosion sensor as a function of the resistance of the corroding element of the witness corrosion sensor, as may apply to the exemplary corrosion sensor 200, according to an aspect of the present application.

FIG. 7 is a graph showing a relation between measured resistance of a witness corrosion sensor as a function of the resistance of the corroding element of the witness corrosion sensor similar to the exemplary corrosion sensor 200, according to an aspect of the present application. As shown in FIG. 7, the horizontal x-axis represents the sheet resistance of the corroding material (e.g., corroding element 103) in units of Ohms/square, and the vertical y-axis represents the sensor resistance in Ohms. The curve 702 illustrates that as the sheet resistance of the corroding material increases, so does the resistance of the sensor. By using a material for the corroding element 103 that has a known resistance curve 702, the rate of corrosion of the material may be assessed and the state of future corrosion determined. Thus, a prediction may be made regarding the corrosion of a target material based on the state of corrosion of the corroding element of the witness corrosion sensor. As a result, the estimated useful life of a target component may be estimated and maintenance or replacement of a target material may be scheduled.

Figure 8:
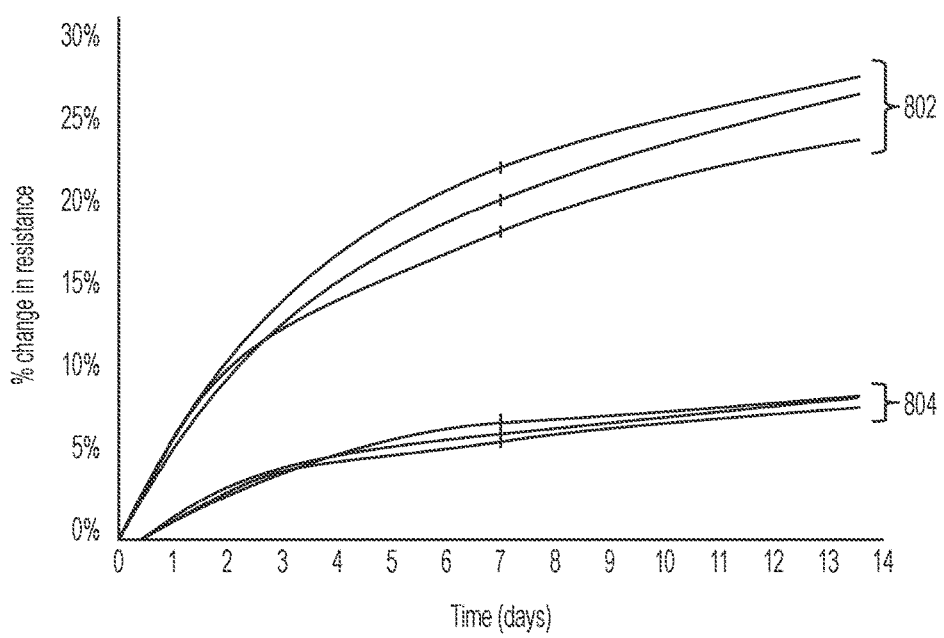
FIG. 8 is a graph showing percentage change in the resistance of a corrosion sensor of the types described herein as a function of elapsed time, according to an aspect of the present application.

FIG. 8 is a graph with curves showing percentage change in the resistance of a corrosion sensor of the types described in FIG. 2 as a function of elapsed time, according to an aspect of the present application. The graph in FIG. 8 illustrates percentage change in resistance as a function of time lapsed from the beginning of a measurement, according to an embodiment. The lapsed time is expressed in days. Curves 802 represent a set of measurements for relative changes of the first resistance of the first resistive arm 101a, while curves 804 represent a set of measurements for relative changes of the second resistance of the second resistive arm 101b in the sensor FIG. 2. Even though the second resistive arm does not have a corroding element exposed to the corrosive environment, the resistances in curves 804 still rises over a time period of 14 days by approximately 8% from their original value. Such a change may be attributed to a background drift of the resistive arm that is not related to corrosion. Therefore the increase of resistance in curves 802 represent a sum of effects from both corrosion of the corroding element 103 and the background drift in the rest of the first resistive arm 101a not subject to corrosion. The difference in percentage change between curves 802 and 804 is caused by corrosion of corroding element 103 and can be processed to indicate the state of corrosion of the target material.

Figure 9:
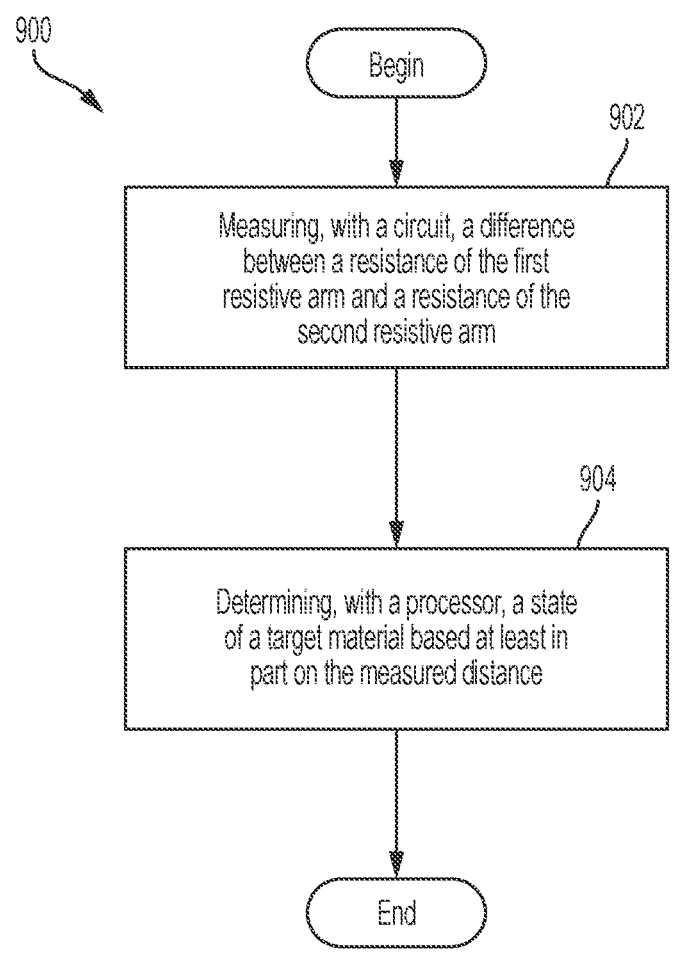
FIG. 9 is a flow diagram showing a method 900 for operating a sensor apparatus of the type shown in FIG. 2, according to an aspect of the present application.

FIG. 9 is a flow diagram showing a method 900 for operating a sensor apparatus similar to the sensor apparatus 100 as shown in FIG. 2, according to an aspect of the present application. Method 900 includes at block 902, the act of measuring, with a circuit, a difference between a resistance of the first resistive arm and a resistance of the second resistive arm and at block 904, the act of determining, with a processor, a state of a target material based at least in part on the measured difference.

Figure 10:
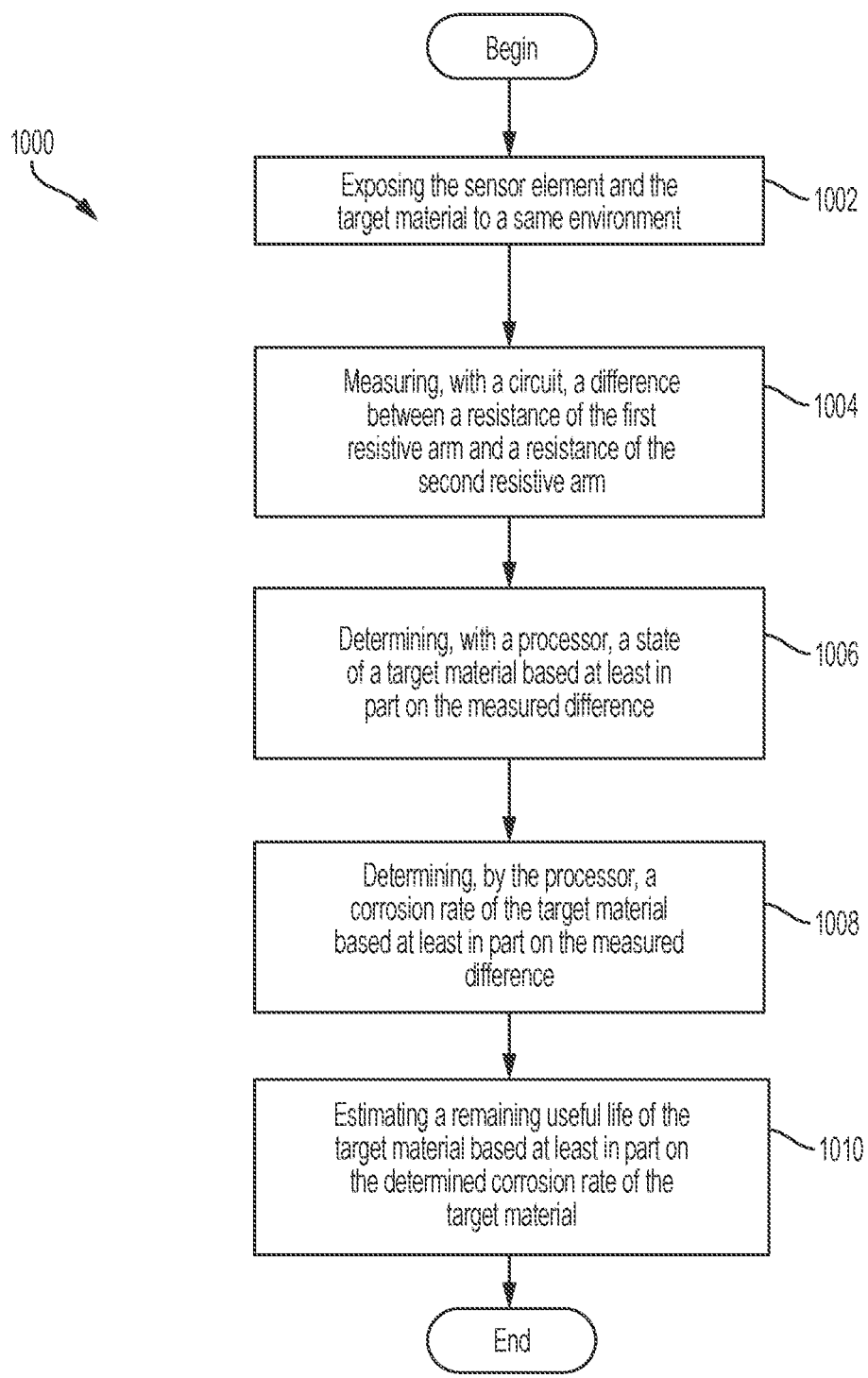
FIG. 10 is a flow diagram showing a method 1000 for operating a sensor apparatus of the type shown in FIG. 2, according to an aspect of the present application.

FIG. 10 is a flow diagram showing a method 1000 for operating a sensor apparatus similar to the sensor apparatus 100 as shown in FIG. 2, according to an aspect of the present application. Method 1000 includes at block 1002, the act of exposing the sensor element and the target material to a same environment; at block 1004, the act of measuring, with a circuit, a difference between a resistance of the first resistive arm and a resistance of the second resistive arm; at block 1006, the act of determining, with a processor, a state of a target material based at least in part on the measured difference; at block 1008, the act of determining, by the processor, a corrosion rate of the target material based at least in part on the measured difference and at block 1010, the act of estimating a remaining useful life of the target material based at least in part on the determined corrosion rate of the target material.

The corrosion sensors described herein may be used to sense the corrosion of various types of target materials and structures. For example, the corrosion sensors may be used in industrial applications to monitor the corrosion of steel, lead, iron, or other materials used in buildings and machinery, as non-limiting examples. The corrosion sensors may be used to monitor the corrosion of automobile and airplane parts, including coatings on such parts. Other uses are possible.

The corrosion sensors described herein may have small dimensions. The use of components formed from CNT structures may facilitate achieving small dimensions. In some embodiments, the corrosion sensors described herein may fit on a single semiconductor chip. In some embodiments, the sensors may be smaller than 5 mm on an edge, less than 3 mm on an edge, or have any value within such ranges.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. A low power wireless sensor system for monitoring a state of corrosion of a target material, the low power wireless sensor system comprising:
    a witness corrosion sensor comprising a first resistive arm with a first resistance and a second resistive arm with a second resistance, the first resistive arm comprising a sensor element and at least one resistor comprising carbon nanotubes, wherein the sensor element is connected in parallel with the at least one resistor comprising carbon nanotubes, and the second resistive arm comprising at least one resistor comprising carbon nanotubes;
    processing circuitry configured to measure a difference between the first resistance and the second resistance and to determine a state of corrosion of the target material based on a difference between the first resistance and the second resistance;
    an energy storage module configured to store electrical energy and to provide power to at least a portion of the processing circuitry; and
    a wireless communication module coupled to the processing circuitry and configured to wirelessly communicate information external to the low power wireless sensor system.

2. The low power wireless sensor system of claim 1, wherein the state of corrosion is an amount of corrosion.

3. The low power wireless sensor system of claim 1, wherein the sensor element has a variable resistance configured to vary based at least in part on a state of corrosion of the sensor element.

4. The low power wireless sensor system of claim 3, wherein the sensor element is configured to be disposed within a same environment as the target material, wherein at least a portion of the second resistive arm is configured to not to be disposed within the same environment.

5. The low power wireless sensor system of claim 4, wherein the sensor element is configured to corrode faster than the target material.

6. The low power wireless sensor system of claim 1, wherein the at least one resistor in the second resistive arm is covered by a non-corroding material.

7. The low power wireless sensor system of claim 1, wherein the information comprises the state of corrosion of the target material.

8. A wireless sensor system for monitoring a state of corrosion of a target material, the wireless sensor system comprising:
    a passive sensor apparatus comprising a first resistive arm with a first resistance and a second resistive arm with a second resistance, the first resistive arm comprising a sensor element and at least one resistor comprising carbon nanotubes, wherein the sensor element is connected in parallel with the at least one resistor comprising carbon nanotubes, and the second resistive arm comprising at least one resistor comprising carbon nanotubes;
    a circuit configured to measure a difference between the first resistance and the second resistance;
    a processor configured to determine a state of corrosion of the target material based on a difference between the first resistance and the second resistance measured by the circuit;

an energy storage module configured to store electrical energy and to provide power to at least a portion of the circuit; and transmit circuitry coupled to the circuit and configured to transmit corrosion information.

9. The wireless sensor system of claim 8, wherein the sensor element is configured to corrode faster than the target material.

10. The wireless sensor system of claim 8, wherein the processor is further configured to estimate a remaining useful life of the target material based at least in part on a corrosion rate of the target material.

11. The wireless sensor system of claim 8, wherein the circuit comprises carbon nanotubes.

12. The wireless sensor system of claim 8, wherein the transmit circuitry is a wireless communication module coupled to the circuit and configured to wirelessly communicate the state of corrosion of the target material.

13. The wireless sensor system of claim 8, wherein the energy storage module comprises an energy harvester.

14. A method for operating a low power wireless sensor system comprising:

measuring, with processing circuitry disposed in the low power wireless sensor system, a difference between a resistance of a first resistive arm and a resistance of a second resistive arm of a witness corrosion sensor comprising the first resistive arm and the second resistive arm, the first resistive arm comprising a sensor element and at least one resistor comprising carbon nanotubes, wherein the sensor element is connected in parallel with the at least one resistor comprising carbon nanotubes, and the second resistive arm comprising at least one resistor comprising carbon nanotubes;

determining, with the processing circuitry, a state of a target material based at least in part on the measured difference;

providing, with an energy storage module configured to store electrical energy, power to at least a portion of the processing circuitry; and wirelessly communicating, with a wireless communication module, information external to the low power wireless sensor system.

15. The method of claim 14, further comprising exposing the sensor element and the target material to a same environment.

16. The method of claim 14, wherein the sensor element has a variable resistance configured to vary in dependence on a state of corrosion of the sensor element.

17. The method of claim 14, wherein the determining comprises estimating a remaining useful life of the target material based at least in part on a corrosion rate of the target material.

18. The method of claim 14, wherein the sensor element is configured to corrode faster than the target material.

19. The method of claim 14, further comprising:

storing energy in the energy storage module with an energy harvester.

20. The method of claim 14, wherein the wirelessly communicating comprises wirelessly transmitting signals representing the measured difference from the processing circuitry to a processor external to the low power wireless sensor system.

* * * * *